United States Patent [19]
Booker et al.

[11] Patent Number: 5,262,646
[45] Date of Patent: Nov. 16, 1993

[54] INFRA-RED SCANNING MICROSCOPY

[76] Inventors: Graham R. Booker; Zsolt J. Laczik; Robert Falster, all of c/o Department of Materials, University of Oxford, Parks Road, Oxford OX1 3PH, Great Britain

[21] Appl. No.: 736,055

[22] Filed: Jul. 26, 1991

[30] Foreign Application Priority Data

Jul. 27, 1990 [GB] United Kingdom ............... 9016587

[51] Int. Cl.⁵ .............................................. G01J 1/00
[52] U.S. Cl. .................................... 250/341; 250/353
[58] Field of Search ............... 250/341, 340, 347, 353; 356/445

[56] References Cited

U.S. PATENT DOCUMENTS

| | | | |
|---|---|---|---|
| 3,624,400 | 11/1971 | Cohen | 250/333 |
| 4,501,966 | 2/1985 | Fosman et al. | 250/332 |
| 4,661,706 | 4/1987 | Messerschmidt et al. | 250/341 |
| 4,843,242 | 6/1989 | Doyle | 250/341 |
| 4,859,064 | 8/1989 | Messerschmidt et al. | 250/341 |

OTHER PUBLICATIONS

IEE Proceedings-I/Solid-State and Electron Devices, vol. 134, No. 3, Part I, Jun. 1987, pp. 85–86, Stevenage, Herts, GB; D. K. Hamliton et al.; "Optical Sectioning in Infra-red Scanning Microscopy".

Primary Examiner—Paul M. Dzierzynski
Assistant Examiner—Richard Hanig
Attorney, Agent, or Firm—Wenderoth, Lind & Ponack

[57] ABSTRACT

A method of assessment of semiconductor wafers by infra-red scanning microscopy illuminates a wafer with infra-red light through its polished face and detects light emanating from the same face by back-scattering from particles within the specimen, the light being back-scattered through an angle of more than 90°. Measures are taken to reduce the effects of specular reflection from the surface, which measures may include the use of stop/mirror arrangements and/or the use of an aperture plate for confocal discrimination.

11 Claims, 6 Drawing Sheets

INFRA-RED SCANNING MICROSCOPY

BACKGROUND OF THE INVENTION

The invention relates to infra-red scanning microscopy and has particular application in the assessment of semiconductor wafers and slabs.

Modern electronic devices are fabricated on electronic grade semiconductor wafers. These are cut from ingots grown from the melt, generally by the Czochralski method. The materials used may be silicon, Group III-V materials such as Gallium-Arsenide or Group II-VI materials such as Cadmium-Telluride.

It is important to be able to assess the quality of the wafers (or slabs) since dislocations occur and there are local precipitations of impurities which may affect the behavior of the material in subsequent heat treatment and which may affect the performance of the electronic devices. A particular problem concerns silicon. Czochralski silicon ingots contain oxygen which has disadvantages and advantages. The principal disadvantage is that in the heat treatment processes associated with the electronic device fabrication, oxygen precipitates out as oxide particles. However, although basically an impurity, the oxide can be used to advantage by careful heat treatment. This is because the oxide particles perform a gettering action on other impurities such as metallic copper. Therefore if, by an annealing process, the oxide particles can be encouraged to precipitate away from a surface on which the electronic devices are to be fabricated, they can be used to draw away other impurities which may be introduced in the fabrication process. Another advantage of the oxygen is that it rigidifies the material.

Thus, the presence of oxide particles can be an advantage in silicon but their number density, size and distribution must be accurately controlled and must therefore be accurately assessed in a given semiconductor wafer. A semiconductor wafer may be 4 to 8 inches in diameter and 0.5 to 1.0 mm in thickness. One surface is polished flat to accept the electronic devices, the other surface is usually 'wavy', and the edge is bevelled. The assessment of wafers is generally by optical microscopy. The wafer is broken and the exposed edge is etched and microscopically examined. This method has the disadvantage that only the exposed surface can be examined and a three-dimensional assessment is not readily possible.

More recently, infra-red imaging techniques have been developed. Semiconductor wafers are transparent to infra-red light. An optimum wavelength for silicon is about 1.3 μm. The light may be produced by a solid state, gas or semiconductor laser and may be focussed to a narrow beam which passes through the wafer. The axis of the laser beam is generally perpendicular to the surface of the wafer. By effecting a scanning movement of either the beam or the wafer in a raster and synchronously interpreting the output of an infra-red detector directed at the wafer, an image can be built up for display on a cathode - ray tube or computer display. Image processing techniques can be used to improve spatial and depth resolution and contrast and alleviate the effects of noise.

Infra-red scanning microscopy can be used in two ways: (a) bright field, or transmission, mode in which the detector looks back along the beam axis and particles in the wafer scatter the light and appear as dark spots against a bright background and (b) dark field, or scattering, mode in which the detector looks obliquely at the wafer and receives light scattered from particles which appear as bright spots against a dark background. Individual particles down to about 30 nm in diameter can be imaged. These techniques have the advantage of being non-destructive of the wafer.

For silicon wafers of these thicknesses, the quality of the image is degraded if the light used to form the image either enters or exits the wafer through a non-flat surface. For bright-field, or for dark-field with the scattering angle less than 90°, high quality images are obtained only if both surfaces of the wafer are polished flat.

A variation of the foregoing technique is to arrange the infra-red detector view the infra-red light at exactly 90° to the incident beam. This is achieved by breaking the wafer and polishing flat the exposed edge at 90° to the polished wafer surface. This technique can produce high quality images. However, it has the disadvantage, along with the etching microscopy method, that the wafer is destroyed in the process of assessment. All that can be assessed, therefore, are wafers which are hopefully similar to those which are to be used in fabrication. It would be an advantage to provide a truly non-destructive method of three-dimensional assessment with satisfactorily high resolution, sensitivity and signal-to-noise ratio. The present invention seeks to provide such a method and a microscope which employs it.

SUMMARY OF THE INVENTION

According to one aspect of the invention there is provided an infra-red scanning microscope comprising a specimen stage for holding a specimen to be examined; a light source arrangement for directing an incident beam of infra-red light at a surface of a specimen held by the specimen stage; scanning means for producing a scanning raster-like relative movement between the beam and the specimen; an infra-red detector arranged to receive light which is back-scattered from the particles within the specimen with a scattering angle greater than 90°; means for synchronously processing the detector output with the scan to produce an image; and a discriminating arrangement whereby the effect of light specularly reflected from the surface of the specimen is reduced with respect to the back-scattered light.

According to another aspect of the invention there is provided a method of assessing a semiconductor specimen having a polished surface by infra-red scanning microscopy which consists in directing a beam of infra-red light into the specimen from the polished surface, producing a scanning raster-like relative movement between the beam and the specimen, detecting infra-red light scattered from particles in the specimen by means of an infra-red detector and synchronously processing the detector output with the scan to produce an image, the detector receiving light which is back-scattered through the polished surface from the particles in the specimen, and taking measures to reduce the effect of light specularly reflected from the surface of the specimen with respect to the back-scattered light.

Thus, in accordance with the invention, the scattering angle (the angle between the incident light and the scattered light, having regard to direction) is greater than 90° and the scattered light emerges from the same surface that the incident light enters. No additional polished flat exit surface is therefore necessary and the required performance can be achieved in a truly non-destructive manner.

Any angle of back-scattering is envisaged, including 180°, with large solid angle detection. A stop/mirror arrangement, perhaps annular, and/or the use of a small aperture in front of the detector (confocal mode arrangement), may be provided so as to receive the light back-scattered by the particles and to not receive or to receive only a small fraction of the light specularly reflected by the surface.

The required relative scanning movement between the beam and the wafer may be achieved by optically manipulating the beam. Preferably, however, the beam remains fixed and there is provided a mechanical device to move the wafer.

BRIEF DESCRIPTION OF THE DRAWINGS

The invention will further be described with reference to the accompanying drawings, of which:

FIG. 1b is a view of the wafer of FIG. 1a from the direction A in FIG. 1a;

DETAILED DESCRIPTION OF THE INVENTION

Figure 1B:
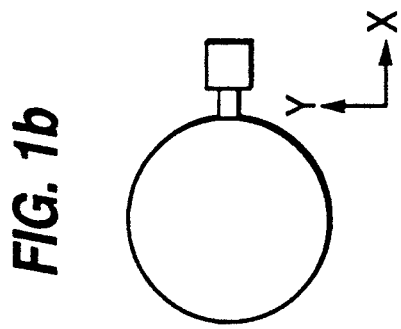
Figure 1A:
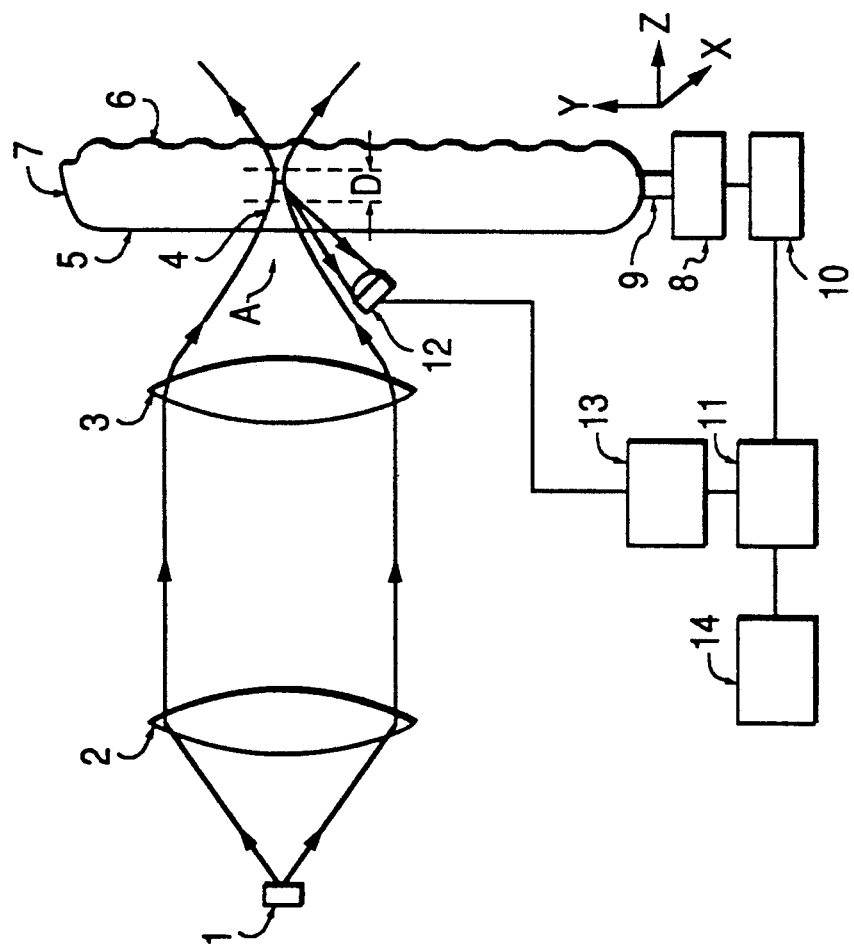
FIG. 1a is a schematic diagram showing the principle of the method in accordance with the invention in assessing a silicon wafer.

Referring to FIGS. 1a and 1b there is shown an infra-red scanning microscope which has an infra-red laser diode 1 which in this example emits light at a wavelength of 1.3 $\mu m$ with a power of 30 mw. The light is focussed by a system consisting of lenses 2 and 3 (a simpler version uses only lens 3) into a silicon wafer to produce a beam 4 in the wafer of a minimum width of about 3 microns extending over an effective depth of field (depth resolution) D of about 30 microns. These parameters can be changed by changing the lens system.

The silicon wafer is of a diameter of some 4 to 8 inches and a thickness of about 0.5 to 1.0 mm. The surface 5 on which the beam 4 is incident is polished flat. The opposite surface 6 is 'wavy' and the edge 7 is bevelled.

A mechanical X-Y-Z drive 8 is coupled to a frame 9 which holds the wafer. The drive is driven by an output from a control unit 10 to move the wafer in a scanning raster relative to the beam. Unit 10 is driven by an output of a system control computer 11.

A detector 12, e.g. germanium diode, is situated on the incident beam side of the wafer to receive light back-scattered from any defects in the wafer illuminated by the beam. In the example shown the back-scattering angle is 135°. It will be seen that the back-scattered light emerges from the polished surface 5. The detector is situated in relation to the incident beam to ensure that little or no light specularly reflected from the surface reaches the detector.

The output after amplification and signal processing from the detector 12 is applied to a circuit 13. The output from the latter circuit is applied to an input of the system control computer 11 where it is synchronously processed with the scan signals to produce an image on the computer display 14.

Figure 2:
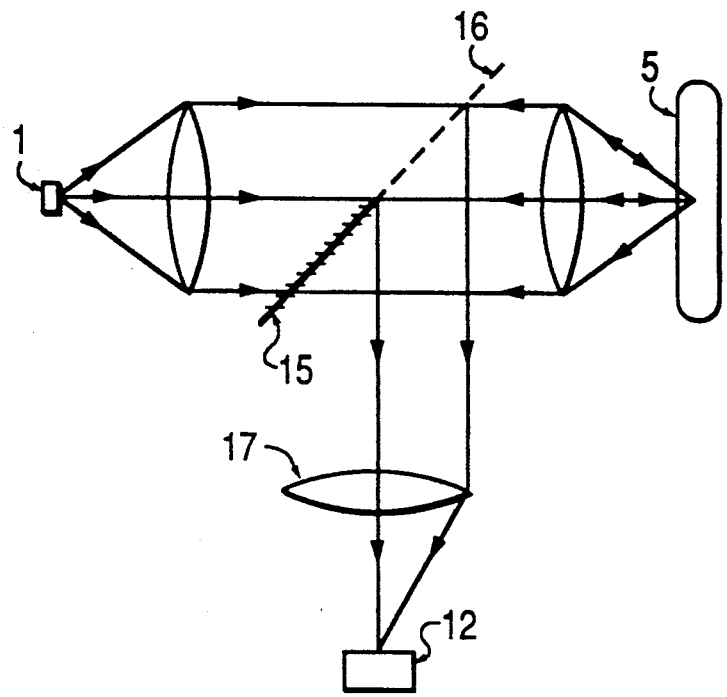
FIG. 2 is a diagram showing an arrangement for a method in accordance with the invention using a half-stop with asymmetrical illumination.

FIG. 2 shows an arrangement whereby detector 12 receives light back-scattered at angles of 145°-180° in a half annular cone with its axis at 180°. A half-stop 15 ensures that light in only half of the cone illuminates the wafer. A beam splitter region 16 has a straight line function with half-stop 15 (i.e. beam splitter 16 is colinear with half-stop 15) and reflects light back-scattered from the specimen but not specularly reflected therefrom. The light from beam-splitter 16 is focussed by a lens 17 onto the detector 12. Light specularly reflected in the other half of the cone is mostly not received by the detector 12.

Figure 3:
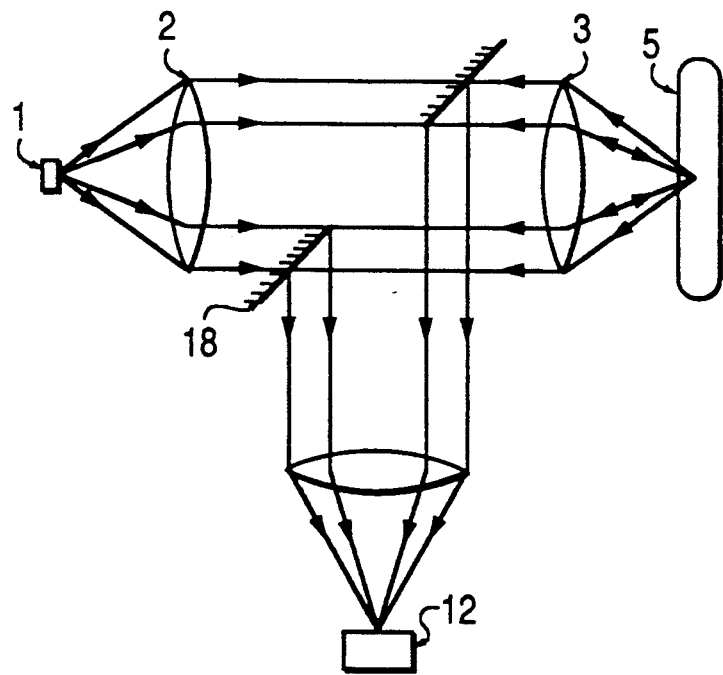
FIG. 3 is a diagram showing an arrangement for a method in accordance with the invention using an annular-stop with inner illumination.

FIG. 3 shows an arrangement whereby detector 12 receives light back-scattered at angles of 125°-180° in an annular cone with its axis at 180°. An aperture stop/mirror 18 ensures that light in only the inner part of the cone illuminates the wafer. Light back-scattered in the outer part of the cone is reflected by the aperture stop/mirror 18 to the detector 12. Light specularly reflected in the inner part of the cone is mostly not received by the detector 12.

Figure 4:
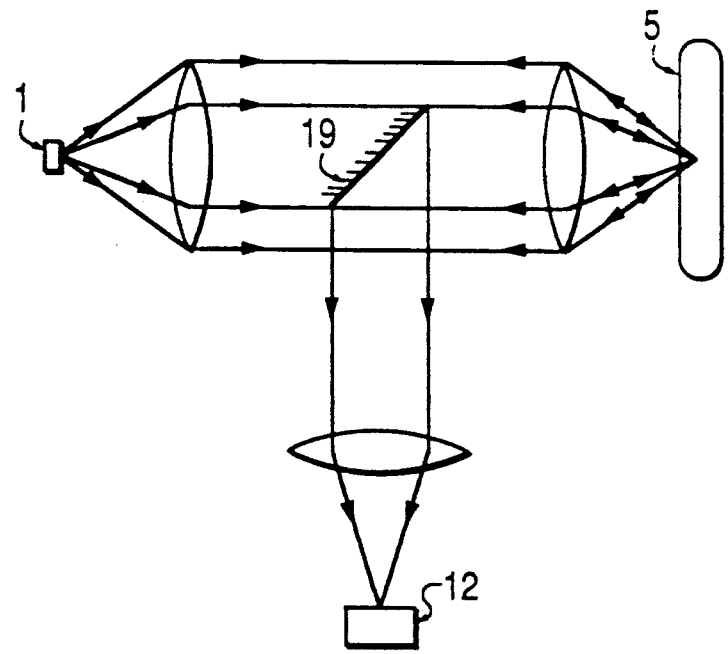
FIG. 4 is a diagram showing an arrangement for a method in accordance with the invention using an annular-stop with outer illumination.

FIG. 4 shows an arrangement whereby detector 12 receives light back-scattered at angles of 125°-180° in an annular cone with its axis at 180°. An aperture stop/mirror 19 ensures that light in only the outer part of the cone illuminates the wafer. Light back-scattered in the inner part of the cone is reflected by the aperture stop/mirror 19 to the detector 12. Light specularly reflected in the outer portion of the cone is mostly not received by the detector 12.

Figure 5:
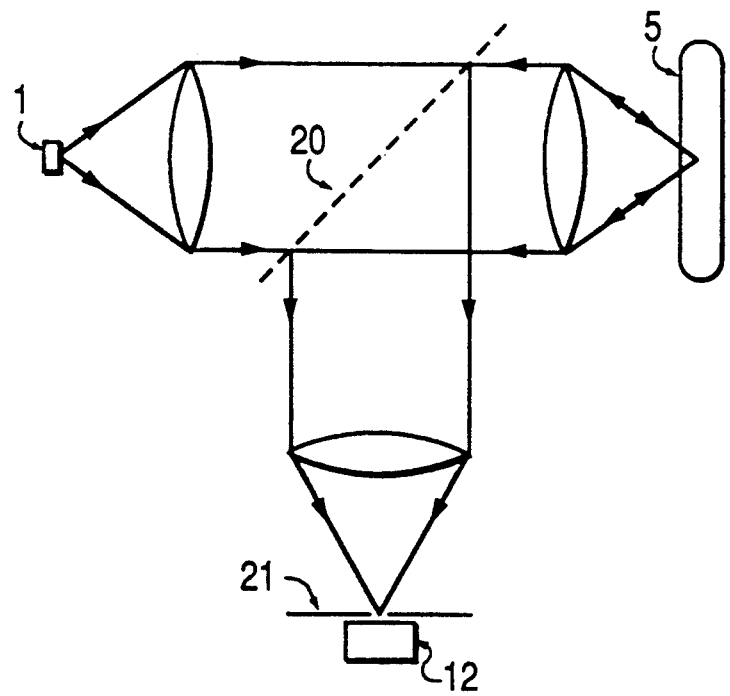
FIG. 5 is a diagram showing an arrangement for a method in accordance with the invention using full illumination and confocal-mode detection.

FIG. 5 shows an arrangement whereby detector 12 receives light back-scattered at angles of 110°-180° in an annular cone with its axis at 180°. A beam splitter 20 ensures that light in the complete cone illuminates the wafer. Light back-scattered in the complete cone, and also light specularly reflected in the complete cone is reflected by the beam-splitter 20 on to the detector 12. A small aperture 21 (typically in the range 5 to 50 $\mu m$ in diameter) is placed in front of the detector 12 and this discriminates between the back-scattered and specularly reflected light received by the detector 12. The small aperture 21 and the detector 12 are positioned so that a large fraction of the back-scattered light and a small fraction of specularly reflected light are received by the detector 12 (confocal mode arrangement). The discrimination occurs because the back-scattered light arises mainly from the position where the incident illumination is focussed within the wafer, while the specularly reflected light arises from the surface of the wafer. This gives rise to two different 'object' positions along the optical axis of the illuminating system and hence two different image positions along the optic axis of the detecting system. The small aperture 21 is placed at the in-focus image of the back-scattered light (large fraction accepted), which corresponds to an out-of-focus image of the specularly reflected light (small fraction accepted).

Figure 6:
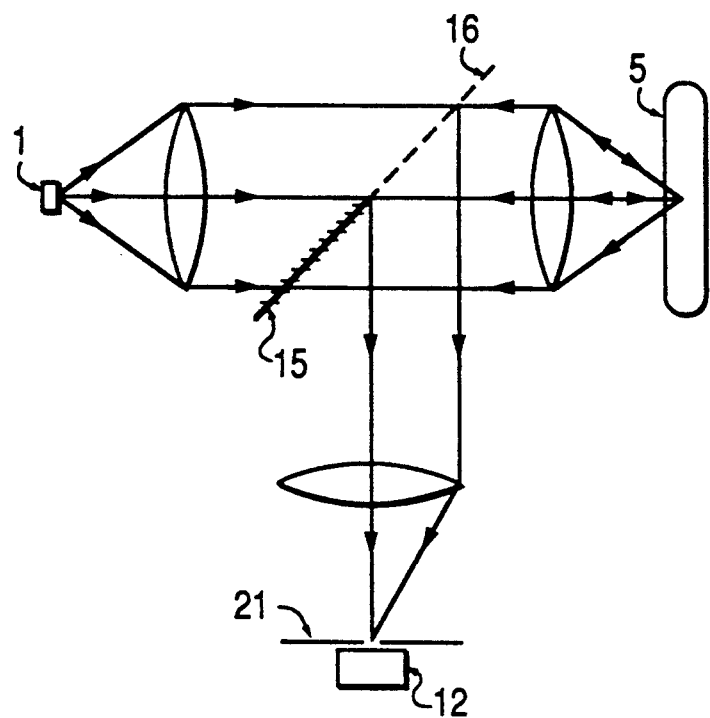
FIG. 6 is a diagram showing an arrangement for a method in accordance with the invention using a half-stop and confocal-mode detection.

FIG. 6 shows an arrangement whereby detector 12 receives light back-scattered at angles of 145°–180° in a half angular cone with its axis at 180°. The difference between this arrangement and that of FIG. 2 is that a small aperture 21 is placed in front of the detector 12. This provides additional discrimination so that the ratio of back-scattered light to specularly reflected light received by the detector 12 is further increased.

Figure 7:
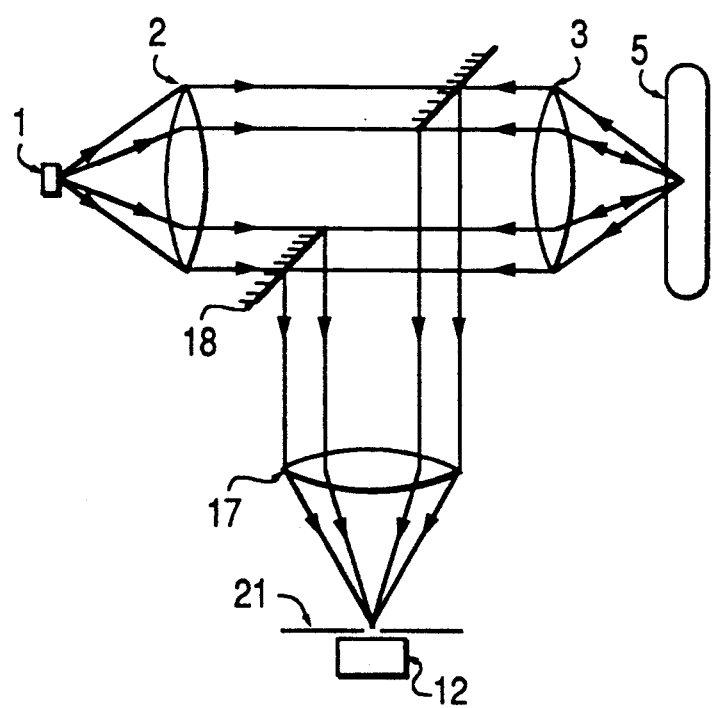
FIG. 7 is a diagram showing an arrangement for a method in accordance with the invention using an annular-stop with inner illumination and confocal ode detection.

FIG. 7 shows an arrangement whereby detector 12 receives light back-scattered at angles of 125°–180° in an annular cone with its axis at 180°. The difference between this arrangement and that of FIG. 3 is that a small aperture 21 is placed in front of the detector 12. This provides additional discrimination so that the ratio of back-scattered light to specularly reflected light received by the detector 12 is further increased.

Figure 8:
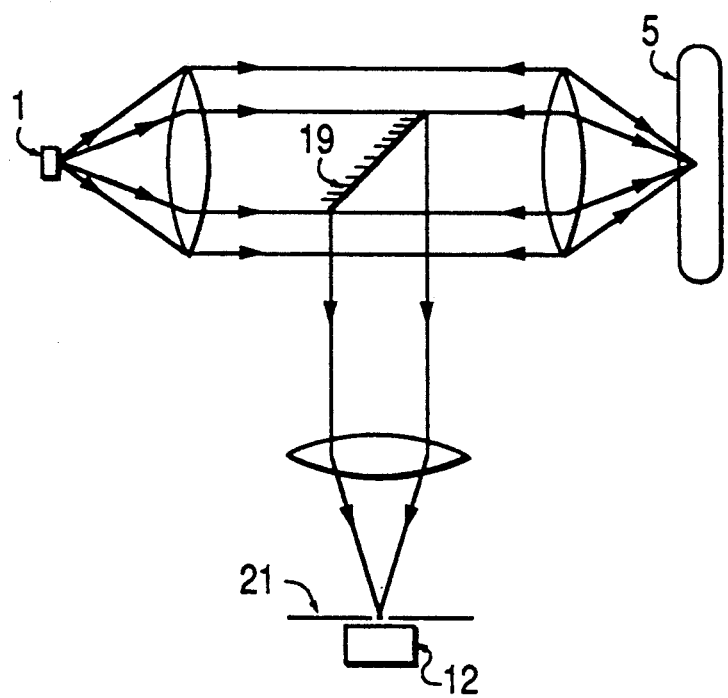
FIG. 8 is a diagram showing an arrangement for a method in accordance with the invention using an annular-stop with outer illumination and confocal mode detection.

FIG. 8 shows an arrangement whereby detector 12 receives light back-scattered at angles 125°–180° in an annular cone with its axis at 180°. The difference between this arrangement and that of FIG. 4 is that a small aperture 21 is placed in front of the detector 12. This provides additional discrimination so that the ratio of back-scattered light to specularly reflected light received by the detector 12 is further increased.

Figure 9:
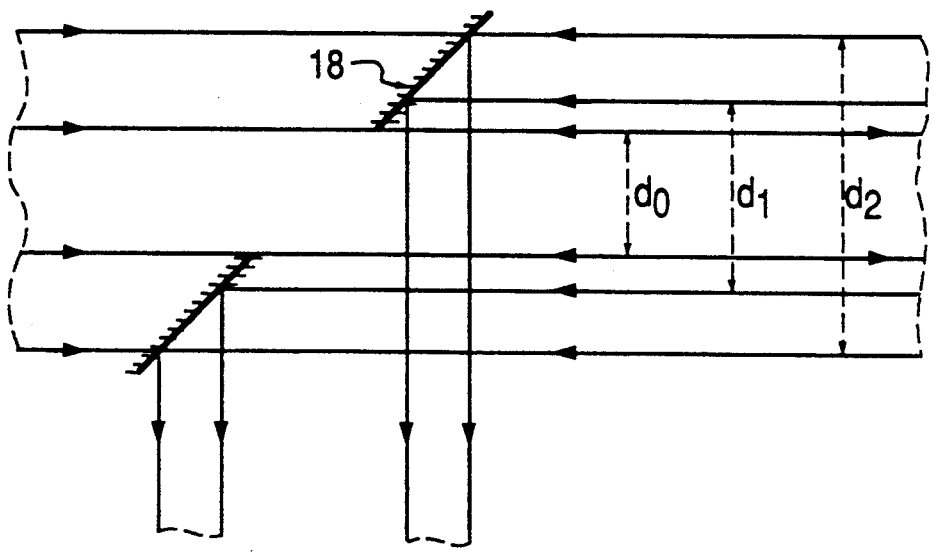
FIG. 9 is a diagram showing part of the arrangement of FIG. 7 after modification.

FIG. 9 shows a modification to the aperture stop of FIG. 7. Of the back-scattered light being reflected by the aperture stop/mirror 18, only that between diameters $d_1$ and $d_2$ is reflected and received by the detector 12, rather than that between diameters $d_o$ and $d_2$ (as in FIG. 7). This modification prevents any specularly reflected light that is present in the marginal region between diameters $d_O$ and $d_1$ from being received by the detector, and this further improves the ratio of back-scattered light to specularly reflected light received by the detector 12.

Figure 10:
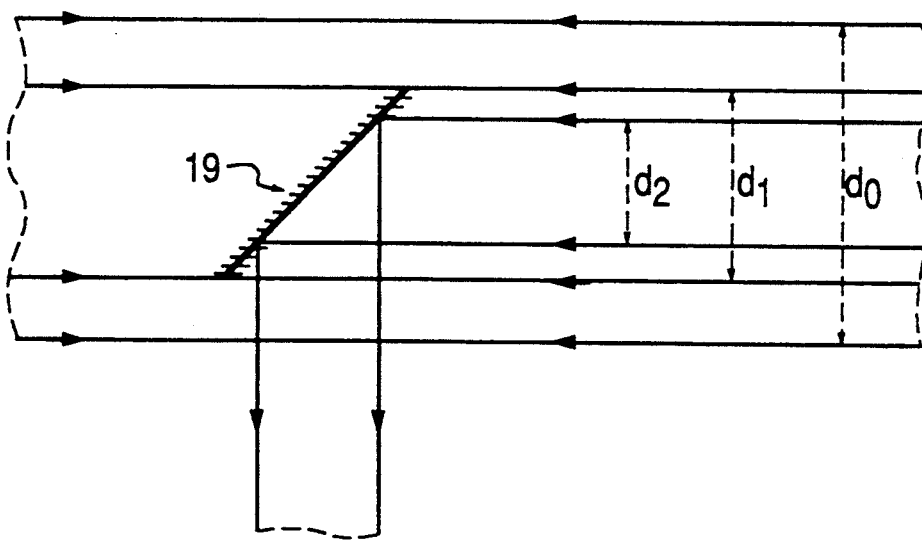
FIG. 10 is a diagram showing part of the arrangement of FIG. 8 after modification.

FIG. 10 shows a modification to the aperture stop of FIG. 8. Of the back-scattered light being reflected by the aperture stop/mirror 19, only that of diameter $d_2$ is reflected and received by the detector 12, rather than that of diameter $d_1$ (as in FIG. 8). This modification prevents any specularly reflected light that is present in the marginal region between diameters $d_1$ and $d_2$ from being received by the detector, and this further improves the ratio of back-scattered light to specularly reflected light received by the detector 12.

For the arrangements shown in FIGS. 3, 4, 7, 8, 9 and 10, the aperture stop/mirror between lenses 2 and 3 both defines the cone of light incident on the wafer, and selects the cone of back-scattered light reflected onto the detector. This aperture stop/mirror can be replaced by a separate stop and mirror. For example, the aperture stop/mirror 18 of FIG. 3 can be replaced by an aperture stop nearer to lens 2 to define the inner incident cone, and a mirror nearer to lens 3 to select the outer back-scattered cone.

The main application parameters for such an infra-red scanning microscope are a) spatial resolution, b) depth of field (depth resolution), c) signal/noise ratio and d) signal back-scattered signal specularly reflected ratio.

The main instrumental parameters that can be used to control the application parameters are, for example, for the arrangement of FIGS. 7 and 9, a) effective numerical aperture (NA) of lens 3, b) effective NA of lens 17, c) diameters $d_O$, $d_1$ and $d_2$ of the aperture stop/mirror 18, and d) the size of aperture 21.

In practice, for a particular materials application, the instrumental parameters are selected to give the optimum performance. For example, when measuring surface denuded zone (SDZ) depths for oxide particles in Czochralski Si wafers after heat treatment as in intrinsic oxide gettering processes, a small depth of field, e.g. 5 $\mu$m, and good elimination of specularly reflected light, are required. This can be achieved by using a high effective NA for lens 3, and a small size aperture 21. Conversely, for a more general investigation of oxide particle number densities and distributions in Cz Si wafers, a larger depth of field, e.g. 30 $\mu$m, and high spatial resolution, e.g. 1 $\mu$m, might be more suitable and elimination of specularly reflected light less important. Different instrumental parameters would then be used.

Three-dimensional information is derived from the wafer by moving the focussed region of the beam within the wafer in the Z direction. Thus, successive X-Y scans are made in respective Z positions to build up a three-dimensional picture. Alternatively cross-sectional variations through the wafer can be assessed by making X-Z scans. This can be achieved by keeping the Y position constant and scanning only in the X direction while moving the focussed region through the wafer in the Z direction.

The present invention has the advantage that actual wafers which are to be used in fabrication can be assessed, since the method is truly non-destructive. The method can also be used for examination during fabrication of the devices and afterward, if desired, to examine the final product.

However, the principal application for the invention is in the assessment of wafers prior to device fabrication and in the control of the crystal growth and annealing conditions.

Although the invention has been described for examining oxide particles in Czochralski Si wafers, it can be similarly applied to other precipitate particles and defects present in other semiconductors, e.g. GaAs, GaP, InP, CdTe, etc. Wafers, slabs and other shaped specimens may be used.

We claim:

1. An infra-red scanning microscope comprising:
   a specimen stage for holding, in a predetermined position, a specimen to be examined;
   a light source means for directing an incident beam of infra-red light toward a surface of the specimen held by said specimen stage, said light source means including a light source;
   scanning means for producing a scanning raster-like movement between the incident beam and the specimen;
   an infra-red detector arranged to receive light back-scattered from particles within the specimen with a scattering angle greater than 90°; and
   discriminating means for allowing back-scatttered light to reach said detector and for preventing a substantial portion of light specularly reflected from the specimen from reaching said detector, said discriminating means comprising a stop/mirror arrangement mounted so as to be disposed in said incident beam and defining a blocking and directing means for blocking a portion of the incident beam from reaching the surface of the specimen held by said specimen stage and for directing back-scattered light toward said detector, focusing means for focussing the back-scattered light directed toward said detector by said stop/mirror arrangement, and an aperture plate positioned between said focussing means and said detector to cause selection of light passing to said detector.

2. An infra-red scanning microscope as recited in claim 1, wherein
said blocking and directing means is operable to cause to be reflected from the specimen a first light region including light specularly reflected from the surface of the specimen and a second light region including back-scattered light from the specimen but little or no light specularly reflected from the surface of the specimen, and to direct to said detector only light from the second light region.

3. An infra-red scanning microscope as recited in claim 2, wherein
said blocking and directing means is operable to block light in a portion of the second light region which is adjacent a border between said first and second light regions.

4. An infra-red scanning microscope as recited in claim 3, wherein
said blocking and directing means includes a mirror positioned to block a central part of the incident beam and to reflect toward said detector a central part of light reflected from the specimen, an annular aperture being formed about said mirror.

5. An infra-red scanning microscope as recited in claim 3, wherein
said blocking and directing means includes an annular mirror positioned to block an outer portion of the incident beam and to reflect toward said detector an output part of light reflected from the specimen, an aperture being formed centrally of said annular mirror.

6. An infra-red scanning microscope as recited in claim 3, wherein
said blocking and directing means includes a first part which is opaque and non-reflective and a second part which is a transmissive and reflective beam splitter;
said first part is arranged to block a portion of the incident beam;
said second part is arranged to allow transmission of a remainder of the incident beam and to reflect to said detector a portion of light reflected from the specimen; and
said first and second parts are colinear.

7. An infra-red scanning microscope as recited in claim 2, wherein
said blocking and directing means includes a mirror positioned to block a central part of the incident beam and to reflect toward said detector a central part of light reflected from the specimen, an annular aperture being formed about said mirror.

8. An infra-red scanning microscope as recited in claim 2, wherein
said blocking and directing means includes an annular mirror positioned to block an outer portion of the incident beam and to reflect toward said detector an outer part of light reflected from the specimen, an aperture being formed centrally of said annular mirror.

9. An infra-red scanning microscope as recited in claim 2, wherein
said blocking and directing means includes a first part which is opaque and non-reflective and a second part which is a transmissive and reflective beam splitter;
said first part is arranged to block a portion of the incident beam;
said second part is arranged to allow transmission of a remainder of the incident beam and to reflect to said detector a portion of light reflected from the specimen; and
said first and second parts are colinear.

10. An infra-red scanning microscope as recited in claim 1, further comprising
means for processing an output from said detector synchronously with the scanning movement produced by said scanning means to produce an image.

11. A method of assessing a semiconductor specimen having a polished surface by infra-red scanning microscopy, comprising:
holding a specimen to be examined in a predetermined position;
directing an incident beam of infra-red light toward the polished surface of the specimen;
producing a scanning raster-like movement between the incident beam and the specimen;
positioning an infra-red detector to receive light back-scattered from particles within the specimen;
preventing a substantial portion of light specularly reflected from the specimen from reaching the detector while allowing back-scattered light to reach the detector, by mounting a stop/mirror arrangement such that it will be disposed in the incident beam and will be effective to block a portion of the incident beam from reaching the polished surface of the specimen and to direct back-scattered light toward the detector, by positioning a focussing means to focus the back-scattered light directed toward the detector by the stop/mirror arrangement, and by positioning an aperture plate between the focussing means and the detector to cause selection of light passing to the detector.

* * * * *